United States Patent
Hoeffkes et al.

(10) Patent No.: US 6,863,698 B1
(45) Date of Patent: Mar. 8, 2005

(54) AGENT FOR DYEING KERATIN CONTAINING FIBERS

(75) Inventors: Horst Hoeffkes, Duesseldorf (DE); David Rose, Hilden (DE); Bernd Meinigke, Leverkusen (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 11 days.

(21) Appl. No.: 10/178,092

(22) Filed: Jun. 24, 2002

Related U.S. Application Data

(63) Continuation of application No. PCT/EP00/12893, filed on Dec. 18, 2000.

(30) Foreign Application Priority Data

Dec. 24, 1999  (DE) ......................................... 199 62 873
Dec. 13, 2000  (DE) ......................................... 100 61 990

(51) Int. Cl.$^7$ ............................................. C09B 67/00
(52) U.S. Cl. ..................... 8/401; 8/405; 8/423; 8/602; 8/688; 548/123; 548/124; 132/202; 132/208
(58) Field of Search .......................... 8/401, 405, 423, 8/602, 688; 132/202, 208; 548/123, 124, 215

(56) References Cited

U.S. PATENT DOCUMENTS

| | | | |
|---|---|---|---|
| 3,749,714 A | 7/1973 | Sato et al. | 260/240.6 |
| 4,865,774 A | 9/1989 | Fabry et al. | 252/549 |
| 4,931,218 A | 6/1990 | Schenker et al. | 252/551 |
| 5,294,726 A | 3/1994 | Behler et al. | 554/98 |
| 5,641,508 A * | 6/1997 | Li et al. | 424/450 |

FOREIGN PATENT DOCUMENTS

| | | |
|---|---|---|
| DE | 37 23 354 | 1/1989 |
| DE | 37 25 030 | 2/1989 |
| DE | 39 26 344 | 2/1991 |
| DE | 197 32 016 | 1/1999 |
| EP | 0 013 257 | 7/1980 |
| EP | 0 873 746 | 10/1998 |
| GB | 1 412 149 | 10/1975 |
| JP | 01-237452 | 9/1989 |

OTHER PUBLICATIONS

Database WPI Derwent Publications, Ltd., London, GB, AN 1989–319875, XP002169922 of JP01237452 (1989).

The Science of Hair Care, Chapter 7, pp. 235–261, published in vol. 7 of Dermatology, Marcel Dekker Inc. NY/Basle (1986).

The Science of Hair Care, Chapter 8, pp. 263–286, published in vol. 7 of Dermatology, Marcel Dekker Inc. NY/Basle (1986).

EU Inventory of Cosmetic Ingredients, Colipa, Mar. 1996 on diskette.

* cited by examiner

*Primary Examiner*—Mark Kopec
*Assistant Examiner*—Eisa Elhilo
(74) *Attorney, Agent, or Firm*—Stephen D. Harper; Gregory M. Hill

(57) ABSTRACT

A method for coloring Keratin-containing fibers which comprises applying a composition containing a compound of formula $$A\text{---}CH\text{=}B\text{---}CH\text{=}A' \qquad \text{(I).}$$

27 Claims, No Drawings

AGENT FOR DYEING KERATIN CONTAINING FIBERS

CROSS REFERENCE TO RELATED APPLICATIONS

This application is a continuation under 35 U.S.C. §365 (c) and §120 of International Application No. PCT/EP00/12893 filed Dec. 18, 2000 and under §119 of German Patent Application Nos. 199 62 873.4 and 100 61 990.8 filed Dec. 24, 1999 and Dec. 13, 2000 respectively.

This invention relates to a composition containing special coloring components for coloring keratin-containing fibers, more particularly human hair, to the use of these special components as coloring components in hair colorants and to a proces for coloring keratin-containing fibers, more particularly human hair.

BACKGROUND OF THE INVENTION

In general, keratin-containing fibers, for example hair, wool or pelts, are dyed either with substantive dyes or with oxidation dyes which are formed by oxidative coupling of one or more primary intermediates with one another or with one or more secondary intermediates. Primary and secondary intermediates are also known as oxidation dye precursors.

The primary intermediates normally used are primary aromatic amines containing another free or substituted hydroxy or amino group in the para or ortho position, diaminopyridine derivatives, heterocyclic hydrazones, 4-aminopyrazolone derivatives and 2,4,5,6-tetraaminopyrimidine and derivatives thereof.

Special representatives are, for example, p-phenylenediamine, p-toluylenediamine, 2,4,5,6-tetraaminopyrimidine, p-aminophenol, N,N-bis-(2'-hydroxyethyl)-p-phenylenediamine, 2-(2',5'-diaminophenyl)-ethanol, 2-(2',5'-diaminophenoxy)-ethanol, 1-phenyl-3-carboxyamido-4-amino-5 pyrazolone, 4-amino-3-methylphenol, 2-aminomethyl-4-aminophenol, 2-hydroxymethyl-4-aminophenol, 2-hydroxy-4,5,6-triaminopyrimidine, 2,4-dihydroxy-5,6-diaminopyrimidine and 2,5,6-triamino-4-hydroxypyrimidine.

The secondary intermediates used are generally m-phenylene-diamine derivatives, naphthols, resorcinol and resorcinol derivatives, pyrazolones, m-aminophenols and substituted pyridine derivatives. Particularly suitable secondary intermediates are α-naphthol, 1,5-, 2,7- and 1,7-dihydroxynaphthalene, 5-amino-2-methylphenol, m-aminophenol, resorcinol, resorcinol monomethyl ether, m-phenylenediamine, 2,4-diaminophenoxyethanol, 2-amino-4-(2'-hydroxyethylamino)-anisole, 1-phenyl-3-methyl-5-pyrazolone, 2,4-dichloro-3-aminophenol, 1,3-bis-(2',4'-diaminophenoxy)-propane, 2-chlororesorcinol, 4-chlororesorcinol, 2-chloro-6-methyl-3-aminophenol, 2-methyl resorcinol, 5-methyl resorcinol 3-amino-6-methoxy-2-methylaminopyridine and 3,5-diamino-2,6-dimethoxypyridine.

With regard to other typical dye components, reference is specifically made to the series entitled "Dermatology" (Editors: Ch. Culnan and H. Maibach), Marcel Dekker Inc., New York/Basel, 1986, Vol. 7, Ch. Zviak, The Science of Hair Care, Chapter 7, pages 248–250 (Substantive Dyes) and Chapter 8, pages 264–267 (Oxidation Dyes) and to the "Europäische Inventar der Kosmetik-Rohstoffe" published by the European Commission and available on floppy disk from the Bundesverband Deutscher Industrie—und Handelsunternehmen für Arzneimittel, Reformwaren und Körperpflegemittel e.V., Mannheim, Germany.

Although intensive colors with good fastness properties can be obtained with oxidation dyes, the color is generally developed under the influence of oxidizing agents, such as $H_2O_2$ for example, which in some cases can result in damage to the fibers. In addition, some oxidation dye precursors or certain mixtures of oxidation dye precursors can occasionally have a sensitizing effect in people with sensitive skin. Although substantive dyes are applied under more moderate conditions, their disadvantage is that, in many cases, the colors obtained often have inadequate fastness properties.

The use of the special components described in more detail hereinafter for coloring keratin-containing fibers has not hitherto been known.

SUMMARY OF THE INVENTION

The problem addressed by the present invention was to provide colorants for keratin fibers, more particularly human hair, which would be at least equivalent in quality to conventional oxidation hair colorants in regard to depth of color, gray coverage and fastness properties, but which would not necessarily have to contain oxidizing agents, such as $H_2O_2$ for example. In addition, the colorants according to the invention would have very little, if any, sensitizing potential.

It has now surprisingly been found that the compounds corresponding to formula I below are eminently suitable for coloring keratin-containing fibers, even in the absence of oxidizing agents. They give a wide variety of colors with excellent brilliance and depth of color. The use of oxidizing agents is not necessary but, in principle, is not ruled out either.

DETAILED DESCRIPTION OF THE INVENTION

The present invention relates to a composition for coloring keratin-containing fibers, more particularly human hair, containing as coloring component compounds corresponding to formula (I):

in which B stands for a group $CR^1$— or a group

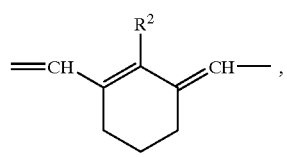

A is selected from the groups:

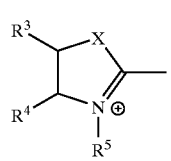

A1

-continued

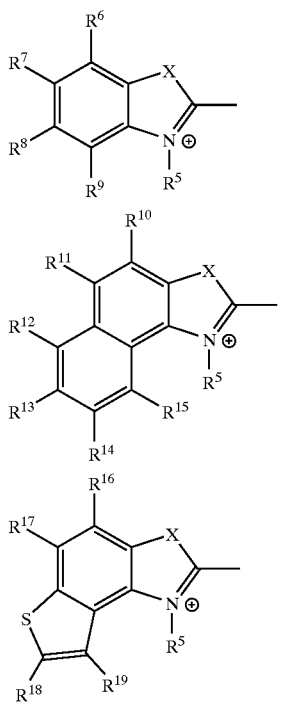

and A' is selected from groups:

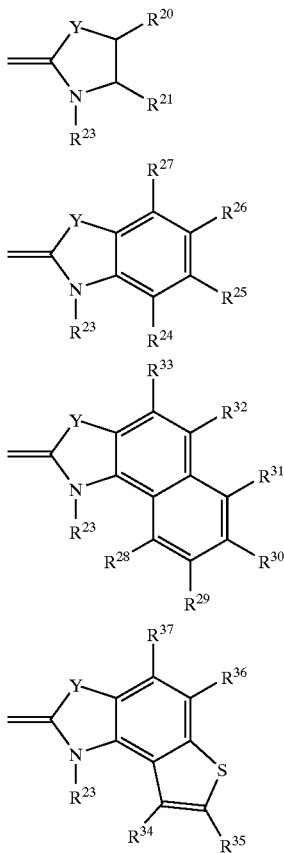

where

X and Y independently of one another represent a sulfur atom, an oxygen atom or a group NR', where R' is a $C_{1-4}$ group optionally substituted by an $SO_3$ group, $R^1$ is hydrogen, a $C_{1-4}$ alkyl group or an $NH_2$ group, $R^2$ is hydrogen or a halogen atom, more particularly a chlorine atom, $R^5$ and $R^{23}$ independently of one another represent a $C_{1-4}$ alkyl group optionally substituted by one or more hydroxy group(s) or an acid or acid anion group, more particularly an $SO_3$ group, $R^8$, $R^{17}$, $R^{25}$ and $R^{26}$ independently of one another represent hydrogen, a $C_{1-4}$ alkyl group, a $C_{1-4}$ alkoxy group, a phenyl group, an $SO_2CF_3$ group or a carboxy group esterified with a $C_{1-4}$ alkyl group, and the other substituents independently of one another are hydrogen, a halogen atom, a $C_{1-4}$ alkyl group or a $C_{1-4}$ alkoxy group optionally substituted by one or more hydroxy groups or halogen atoms, the positive charge being compensatable by a negative charge in one of the substituents or by an acid anion.

In the context of the invention, keratin-containing fibers are understood to include wool, pelts, feathers and, in particular, human hair. In principle, however, the colorants according to the invention may also be used to color other natural fibers such as, for example, cotton, jute, sisal, linen or silk, modified natural fibers such as, for example, regenerated cellulose, nitro, alkyl or hydroxyalkyl or acetyl cellulose and synthetic fibers such as, for example, polyamide, polyacrylonitrile, polyurethane and polyester fibers.

Examples of the $C_{1-4}$ alkyl groups mentioned as substituents in the compounds according to the invention are the methyl, ethyl, propyl, isopropyl and butyl groups. Ethyl and methyl groups are preferred alkyl groups. According to the invention, preferred $C_{1-4}$ alkoxy radicals are, for example, methoxy or ethoxy groups. Other preferred examples of a $C_{1-4}$ hydroxyalkyl group are the hydroxymethyl, 2-hydroxyethyl, 3-hydroxypropyl or 4-hydroxybutyl group. A 2-hydroxyethyl group is particularly preferred. According to the invention, examples of a halogen atom are the F, Cl or Br atom. A Cl atom is most particularly preferred. According to the invention, the other terms used are derived from the definitions given here.

According to the invention, particularly preferred compounds of formula I are those in which $R^5$ and $R^{23}$ independently of one another represent a methyl group, an ethyl group, a 2-hydroxyethyl group or a 2-sulfonate propyl group.

Other particularly preferred compounds of formula I are those in which $R^8$, $R^{17}$, $R^{25}$ and $R^{26}$ independently of one another represent hydrogen, a methyl group, an ethyl group, a methoxy group, a phenyl group, an $SO_2CF_3$ group or a carboxyethyl group.

A particularly preferred embodiment of the present invention is characterized by the use of one or more of the compounds mentioned in Table 1 as the compounds of formula I (the substituents not defined in the Table represent hydrogen).

TABLE 1.1

| | A | X | $R^5$ | B | A' | Y | $R^{23}$ | Counterion |
|---|---|---|---|---|---|---|---|---|
| Compound 1 | A1 | S | $CH_3$ | =CH— | A14 | S | $C_2H_5$ | Iodide |
| Compound 2 | A1 | S | $CH_3$ | =CH— | A14 | S | 3-Sulfonatepropyl | — |
| Compound 3 | A1 | S | $CH_3$ | =CH— | A12 | S | 3-Sulfonatepropyl | — |
| Compound 4 | A1 | S | $CH_3$ | =CH— | A13 | S | 3-Sulfonatepropyl | — |
| Compound 5 | A1 | S | $CH_3$ | =CH— | A12 | S | $C_2H_5$ | Iodide |
| Compound 6 | A1 | S | $CH_3$ | =CH— | A13 | S | $CH_3$ | Iodide |
| Compound 7 | A3 | S | 3-Sulfonate-propyl | $CR^1$ $R^1 = C_2H_5$ | A13 | S | 3-Sulfonatepropyl | Pyridinum |
| Compound 8 | A2 | S | 3-Sulfonate-propyl | $CR^1$ $R^1 = NH_2$ | A12 | S | 3-Sulfonatepropyl | Ammonium |
| Compound 9 | A2 $R^8 = COOC_2H_5$ | N—$C_2H_5$ | $C_2H_5$ | =CH— | A12 $R^{26} = COOC_2H_5$ | (3-Sulfonate-propyl)-N | $C_2H_5$ | — |

TABLE 1.2

| | A | X | $R^5$ | B | A' | Y | $R^{23}$ | Counterion |
|---|---|---|---|---|---|---|---|---|
| Compound 10 | A2 $R^8 = SO_2CF_3$ | N—$C_2H_5$ | $C_2H_5$ | =CH— | A12 $R^{25} = SO_2CF_3$ | N—$C_2H_5$ | $C_2H_5$ | Iodide |
| Compound 11 | A2 | S | 2-Hydroxyethyl | $CR^1$ $R^1 = CH_3$ | A12 | S | 2-Hydroxyethyl | Chloride |
| Compound 12 | A3 | S | 3-Sulfonate-propyl | $CR^1$ $R^1 = C_2H_5$ | A12 $R^{25} = OCH_3$ | S | $C_2H_5$ | — |
| Compound 13 | A4 | S | 3-Sulfonate-propyl | $CR^1$ $R^1 = C_2H_5$ | A14 | S | 3-Sulfonate-propyl | Pyridinium |
| Compound 14 | A4 $R^{17} = OCH_3$ | S | 3-Sulfonate-propyl | $CR^1$ $R^1 = C_2H_5$ | A12 $R^{25} = Phenyl$ | S | 3-Sulfonate-propyl | Triethylammonium |
| Compound 15 | A4 | S | 3-Sulfonate-propyl | $CR^1$ $R^1 = C_2H_5$ | A12 $R^{25} = OCH_3$ | S | $C_2H_5$ | — |
| Compound 16 | A3 | S | 3-Sulfonate-propyl | $CR^1$ $R^1 = C_2H_5$ | A14 | S | 3-Sulfonate-propyl | Triethylammonium |
| Compound 17 | A2 $R^8 = Phenyl$ | O | $C_2H_5$ | $CR^1$ $R^1 = C_2H_5$ | A12 $R^{25} = Phenyl$ | O | $C_2H_5$ | Ethylsulfate |
| Compound 18 | A1 | S | $C_2H_5$ | =CH— | A11 | S | $C_2H_5$ | Iodide |

TABLE 1.3

| | A | X | $R^5$ | B | A' | Y | $R^{23}$ | Counterion |
|---|---|---|---|---|---|---|---|---|
| Compound 19 | A2 $R^8 = OCH_3$ | S | 2-Hydroxy-ethyl | $CR^1$ $R^1 = C_2H_5$ | A12 $R^{25} = OCH_3$ | S | 2-Hydroxy-ethyl | 4-Methylbenzene sulfonate |
| Compound 20 | A3 | S | $CH_3$ | $CR^1$ $R^1 = CH_3$ | A13 | S | $CH_3$ | Iodide |
| Compound 21 | A2 $R^8 = Phenyl$ | O | $C_2H_5$ | $CR^1$ $R^1 = CH_3$ | A12 $R^{25} = Phenyl$ | O | $C_2H_5$ | Ethylsulfate |
| Compound 22 | A2 | S | $C_2H_5$ | 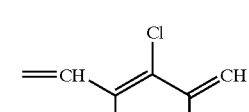 | A12 | S | $C_2H_5$ | Iodide |
| Compound 23 | A2 | S | $C_2H_5$ | $CR^1$ $R^1 = CH_3$ | A12 | S | $C_2H_5$ | Iodide |
| Compound 24 | A2 $R^8 = Phenyl$ | O | 3-Sulfonate-propyl | $CR^1$ $R^1 = C_2H_5$ | A12 $R^{25} = Phenyl$ | O | 3-Sulfonate propyl | Pyridinium |

Preferred acid anions for compensating the positive charge are acid anion groups in the compounds of formula I themselves or free anions, more particularly benzenesulfonate, p-toluenesulfonate, methanesulfonate, ethanesulfonate, propanesulfonate, perchlorate, sulfate, chloride, bromide, iodide, tetrachlorozincate, methylsulfates, trifluoromethanesulfonate, hexafluorophosphate and/or tetrafluoroborate.

The compounds corresponding to formula I are partly known from the literature, commercially available or obtainable by known synthesis methods.

The above-mentioned compounds of formula I are used in the compositions according to the invention in a quantity of preferably 0.03 to 65 mmol and more particularly 1 to 40 mmol, based on 100 g of the colorant as a whole.

The compounds of formula I used in accordance with the invention may be used as substantive colorants or in the presence of typical oxidation dye precursors, such as typical primary and secondary intermediates of the type mentioned in the preamble to this specification.

Colorants which contain the compounds according to the invention as sole coloring component are preferably used for colors ranging from yellow through orange to red.

In order to obtain further and more intensive colors, the colorants according to the invention may additionally contain color intensifiers. The color intensifiers are preferably selected from the group consisting of piperidine, piperidine-2-carboxylic acid, piperidine-3-carboxylic acid, piperidine-4-carboxylic acid, pyridine, 2-hydroxypyridine, 3-hydroxypyridine, 4-hydroxypyridine, imidazole, 1-methyl imidazole, histidine, pyrrolidine, proline, pyrrolidone, pyrrolidone-5-carboxylic acid, pyrazole, 1,2,4-triazole, piperazine, derivatives and physiologically compatible salts thereof.

The color intensifiers mentioned above may be used in a quantity of 0.03 to 65 mmol and more particularly 1 to 40 mmol, based on 100 g of the colorant as a whole.

In all colorants, several different compounds corresponding to formula I may also be used. Similarly, several different oxidation dye precursors and/or color intensifiers may also be used together.

Oxidizing agents, for example $H_2O_2$, need not present. However, it may be desirable in some cases to add hydrogen peroxide or other oxidizing agents to the compositions according to the invention to obtain shades which are lighter than the keratin-containing fibers to be colored. Oxidizing agents are generally used in a quantity of 0.01 to 6% by weight, based on the solution applied. A preferred oxidizing agent for human hair is $H_2O_2$.

In one preferred embodiment, the colorants according to the L, invention contain typical substantive dyes in addition to the compounds present in accordance with the invention in order further to modify the color tones. The substantive dyes may be selected, for example, from the group of nitrophenylenediamines, nitroaminophenols, anthraquinones or indophenols such as, for example, the compounds known under the International names or commercial names of HC Yellow 2, HC Yellow 4, HC Yellow 6, Basic Yellow 57, Disperse Orange 3, HC Red 3, HC Red BN, Basic Red 76, HC Blue 2, Disperse Blue 3, Basic Blue 99, HC Violet 1, Disperse Violet 1, Disperse Violet 4, Disperse Black 9, Basic Brown 16 and Basic Brown 17, picramic acid, 2-amino-6-chloro-4-nitrophenol, 4-amino-2-nitrodiphenylamine-2'-carboxylic acid, 6-nitro-1,2,3,4-tetrahydroquinoxaline, 4-N-ethyl-1,4-bis-(2'-hydroxyethylamino)-2-nitrobenzene hydrochloride and 1-methyl-3-nitro-4-(2'-hydroxyethyl)-aminobenzene. The compositions according to the invention in this embodiment contain the substantive dyes in a quantity of, preferably, 0.01 to 20% by weight, based on the colorant as a whole.

The preparations according to the invention may also contain naturally occurring dyes such as, for example, henna red, henna neutral, henna black, camomile blossom, sandalwood, black tea, black alder bark, sage, logwood, madder root, catechu, sedre and alkanet.

The compounds of formula I present in accordance with the invention or the oxidation dye precursors, color intensifiers and substantive dyes optionally present do not have to be single compounds. On the contrary, other components may be present in small quantities in the hair colorants according to the invention due to the processes used to produce the individual dyes providing these other components do not adversely affect the coloring result or have to be ruled out for other reasons, for example toxicological reasons.

The colorants according to the invention produce intensive colors even at physiologically compatible temperatures of <45° C. Accordingly, they are particularly suitable for coloring human hair. For application to human hair, the colorants are normally incorporated in a water-containing cosmetic carrier. Suitable water-containing cosmetic carriers are, for example, creams, emulsions, gels or even surfactant-containing foaming solutions, for example shampoos or other formulations suitable for application to the keratin-containing fibers. If necessary, the colorants may even be incorporated in water-free carriers.

The colorants according to the invention may also contain any of the known active substances, additives and auxiliaries typical of such preparations. In many cases, the colorants contain at least one surfactant, both anionic and zwitterionic, ampholytic, nonionic and cationic surfactants being suitable in principle. In many cases, however, it has been found to be of advantage to select the surfactants from anionic, zwitterionic or nonionic surfactants.

Suitable anionic surfactants for the compositions according to the invention are any anionic surface-active substances suitable for use on the human body. Such substances are characterized by a water-solubilizing anionic group such as, for example, a carboxylate, sulfate, sulfonate or phosphate group and a lipophilic alkyl group containing around 10 to 22 carbon atoms. In addition, glycol or polyglycol ether groups, ester, ether, amide groups and hydroxyl groups may also be present in the molecule. The following are examples of suitable anionic surfactants—in the form of the sodium, potassium and ammonium salts and the mono-, di- and trialkanolammonium salts containing 2 or 3 carbon atoms in the alkanol group:

linear fatty acids containing 10 to 22 carbon atoms (soaps), ether carboxylic acids corresponding to the formula $R-O-(CH_2-CH_2O)_x-CH_2-COOH$, in which R is a linear alkyl group containing 10 to 22 carbon atoms and x=0 or 1 to 16, acyl sarcosides containing 10 to 18 carbon atoms in the acyl group, acyl taurides containing 10 to 18 carbon atoms in the acyl group, acyl isethionates containing 10 to 18 carbon atoms in the acyl group, sulfosuccinic acid mono- and dialkyl esters containing 8 to 18 carbon atoms in the alkyl group and sulfosuccinic acid monoalkyl polyoxyethyl esters containing 8 to 18 carbon atoms in the alkyl group and 1 to 6 oxyethyl groups, linear alkane sulfonates containing 12 to 18 carbon atoms, linear α-olefin sulfonates containing 12 to 18 carbon atoms, α-sulfofatty acid methyl esters of fatty acids containing 12 to 18 carbon atoms, alky sulfates and alkyl polyglycol ether sulfates corresponding to the formula $R-O(CH_2-CH_2O)_x-SO_3H$, in which R is a preferably linear alkyl group containing 10 to 18 carbon atoms and x=0 or 1 to 12, mixtures of surface-active hydroxysulfonates according to DE-A-37 25 030, sulfated hydroxyalkyl polyethylene and/or hydroxyalkylene propylene glycol ethers according to DE-A-37 23 354, sulfonates of unsaturated fatty acids containing 12 to 24 carbon atoms and 1 to 6 double bonds according to DE-A-39 26 344, esters of tartaric acid and citric acid with alcohols in the form of addition products of around 2 to 15 molecules of ethylene oxide and/or propylene oxide with fatty alcohols containing 8 to 22 carbon atoms.

Preferred anionic surfactants are alkyl sulfates, alkyl polyglycol ether sulfates and ether carboxylic acids containing 10 to 18 carbon atoms in the alkyl group and up to 12 glycol ether groups in the molecule and, in particular, salts of saturated and, more particularly, unsaturated $C_{8-22}$ carboxylic acids, such as oleic acid, stearic acid, isostearic acid and palmitic acid.

In the context of the invention, zwitterionic surfactants are surface-active compounds which contain at least one quaternary ammonium group and at least one $—COO^{(-)}$ or $—SO_3^{(-)}$ group in the molecule. Particularly suitable zwitterionic surfactants are the so-called betaines, such as N-alkyl-N,N-dimethyl ammonium glycinates, for example coconut alkyl dimethyl ammonium glycinate, N-acylaminopropyl-N,N-dimethyl ammonium glycinates, for example coconut acylaminopropyl dimethyl ammonium glycinate, and 2-alkyl-3-carboxymethyl-3-hydroxyethyl imidazolines containing 8 to 18 carbon atoms in the alkyl or acyl group and coconut acylaminoethyl hydroxyethyl carboxymethyl glycinate. A preferred zwitterionic surfactant is the fatty acid amide derivative known by the CTFA name of Cocamidopropyl Betaine.

Ampholytic surfactants are surface-active compounds which, in addition to a $C_{8-18}$ alkyl or acyl group, contain at least one free amino group and at least one —COOH or —SO₃H group in the molecule and which are capable of forming inner salts. Examples of suitable ampholytic surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids containing around 8 to 18 carbon atoms in the alkyl group. Particularly preferred ampholytic surfactants are N-coconutalkyl aminopropionate, coconutacyl aminoethyl aminopropionate and $C_{12-18}$ acyl sarcosine.

Nonionic surfactants contain, for example, a polyol group, a poly-alkylene glycol ether group or a combination of polyol and polyglycol ether groups as the hydrophilic group. Examples of such compounds are products of the addition of 2 to 30 moles of ethylene oxide and/or 0 to 5 moles of propylene oxide onto linear fatty alcohols containing 8 to 22 carbon atoms, onto fatty acids containing 12 to 22 carbon atoms and onto alkylphenols containing 8 to 15 carbon atoms in the alkyl group, $C_{12-22}$ fatty acid monoesters and diesters of products of the addition of 1 to 30 moles of ethylene oxide onto glycerol, $C_{8-22}$ alkyl mono- and oligoglycosides and ethoxylated analogs thereof, products of the addition of 5 to 60 moles of ethylene oxide onto castor oil and hydrogenated castor oil, products of the addition of ethylene oxide onto sorbitan fatty acid esters, products of the addition of ethylene oxide onto fatty acid alkanolamides.

Examples of cationic surfactants suitable for use in the hair treatment formulations according to the invention are, in particular, quaternary ammonium compounds. Preferred quaternary ammonium compounds are ammonium halides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. Other cationic surfactants suitable for use in accordance with the invention are the quaternized protein hydrolyzates.

Also suitable for use in accordance with the invention are cationic silicone oils such as, for example, the commercially available products Q2-7224 (manufacturer: Dow Corning; a stabilized trimethyl silyl amodimethicone), Dow Corning 929 Emulsion (containing a hydroxylamino-modified silicone which is also known as amodimethicone), SM-2059 (manufacturer: General Electric), SLM-55067 (manufacturer: Wacker) and Abil®-Quat 3270 and 3272 (manufacturer: Th. Goldschmidt; diquaternary polydimethyl siloxanes, quaternium-80).

Alkyl amidoamines, particularly fatty acid amidoamines, such as the stearyl amidopropyl dimethyl amine obtainable as Tego Amid®S 18, are distinguished not only by their favorable conditioning effect, but also and in particular by their ready biodegradability.

Quaternary ester compounds, so-called "esterquats", such as the methyl hydroxyalkyl dialkoyloxyalkyl ammonium methosulfates marketed under the trade name of Stepantex®, are also readily biodegradable.

One example of a quaternary sugar derivative suitable for use as a cationic surfactant is the commercially available product Glucquat®100 (CTFA name: Lauryl Methyl Gluceth-10 Hydroxypropyl Dimonium Chloride).

The compounds containing alkyl groups used as surfactants may be single compounds. In general, however, these compounds are produced from native vegetable or animal raw materials so that mixtures with different alkyl chain lengths dependent upon the particular raw material are obtained.

The surfactants representing addition products of ethylene and/or propylene oxide with fatty alcohols or derivatives of these addition products may be both products with a "normal" homolog distribution and products with a narrow homolog distribution. Products with a "normal" homolog distribution are mixtures of homologs which are obtained in the reaction of fatty alcohol and alkylene oxide using alkali metals, alkali metal hydroxides or alkali metal alcoholates as catalysts. By contrast, narrow homolog distributions are obtained when, for example, hydrotalcites, alkaline earth metal salts of ether carboxylic acids, alkaline earth metal oxides, hydroxides or alcoholates are used as catalysts. The use of products with a narrow homolog distribution can be of advantage.

Other active substances, auxiliaries and additives are, for example, nonionic polymers such as, for example, vinyl pyrrolidonelvinyl acrylate copolymers, polyvinyl pyrrolidone and vinyl pyrrolidonelvinyl acetate copolymers and polysiloxanes, cationic polymers, such as quaternized cellulose ethers, polysiloxanes containing quaternary groups, dimethyl diallyl ammonium chloride polymers, acrylamide/dimethyl diallyl ammonium chloride copolymers, dimethyl aminoethyl methacrylate/vinyl pyrrolidone copolymers quaternized with diethyl sulfate, vinyl pyrrolidone/imidazolinium methochloride copolymers and quaternized polyvinyl alcohol, zwitterionic and amphoteric polymers such as, for example, acrylamido-propyl/trimethyl ammonium chloride/acrylate copolymers and octyl acrylamide/methyl methacrylate/tert.butyl aminoethyl methacrylate/2-hydroxypropyl methacrylate copolymers, anionic polymers such as, for example, polyacrylic acids, crosslinked polyacrylic acids, vinyl acetate/crotonic acid copolymers, vinyl pyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert.butyl acrylamide terpolymers, thickeners, such as agar agar, guar gum, alginates, xanthan gum, gum arabic, karaya gum, locust bean gum, linseed gums, dextrans, cellulose derivatives, for example methyl cellulose, hydroxyalkyl cellulose and carboxymethyl cellulose, starch fractions and derivatives, such as amylose, amylopectin and dextrins, clays such as, for example, bentonite or fully synthetic hydrocolloids such as, for example, polyvinyl alcohol, structurants, such as glucose and maleic acid, hair-conditioning compounds, such as phospholipids, for example soya lecithin, egg lecithin and kephalins, and also silicone oils, protein hydrolyzates, more particularly elastin, collagen, keratin, milk protein, soya protein and wheat protein hydrolyzates, condensation products thereof with fatty acids and quaternized protein hydrolyzates, perfume oils, dimethyl isosorbide and cyclodextrins, solubilizers, such as ethanol, isopropanol, ethylene glycol, propylene glycol, glycerol and diethylene glycol, antidandruff agents, such as Piroctone Olamine and Zinc Omadine, other substances for adjusting the pH value, active substances, such as panthenol, pantothenic acid, allantoin, pyrrolidone carboxylic acids and salts thereof, plant extracts and vitamins, cholesterol, sun protection factors, consistency factors, such as sugar esters, polyol esters or polyol alkyl ethers, fats and waxes, such as spermaceti, beeswax, montan wax, paraffins, fatty alcohols and fatty acid esters, fatty acid alkanolamides, complexing agents, such as EDTA, NTA and phosphonic acids, swelling and penetration agents, such as glycerol, propylene glycol monoethyl ether, carbonates, hydrogen carbonates, guanidines, ureas and primary, secondary and tertiary phosphates, imidazoles, tannins, pyrrole, opacifiers, such as latex, pearlizers, such as ethylene glycol mono- and distearate, propellents, such as propane/butane mixtures, $N_2O$, dimethyl ether, $CO_2$ and air and antioxidants.

To produce the colorants according to the invention, the constituents of the water-containing carrier are used in the usual quantities for this purpose. For example, emulsifiers are used in concentrations of 0.5 to 30% by weight while thickeners are used in concentrations of 0.1 to 25% by weight, based on the colorant as a whole.

It can be of advantage to the coloring result to add ammonium or metal salts to the colorants. Suitable metal salts are, for example, formates, carbonates, halides, sulfates, butyrates, valerates, caproates, acetates, lactates, glycolates, tartrates, citrates, gluconates, propionates, phosphates and phosphonates of alkali metals, such as potassium, sodium or lithium, alkaline earth metals, such as magnesium, calcium, strontium or barium, or of aluminium, manganese, iron, cobalt, copper or zinc, sodium acetate, lithium bromide, calcium bromide, calcium gluconate, zinc chloride, zinc sulfate, magnesium chloride, magnesium sulfate, ammonium carbonate, chloride and acetate being preferred. These salts are preferably present in a quantity of 0.03 to 65 mmol and more preferably in a quantity of 1 to 40 mmol, based on 100 g of the colorant as a whole. The pH value of the ready-to-use coloring preparations is normally in the range from 2 to 12 and preferably in the range from 4 to 10.

In a second embodiment, the present invention relates to the use of the compounds of formula I for coloring keratinous fibers.

In a third embodiment, the present invention relates to a process for coloring keratin-containing fibers, more particularly human hair, in which a colorant containing at least one compound corresponding to formula I and typical cosmetic ingredients is applied to the keratin-containing fibers, left thereon for a while, typically ca. 30 minutes, and then rinsed out again or washed out with a shampoo.

The compounds for formula I and the oxidation dye precursors, color intensifiers and substantive dyes optionally present may either be applied to the hair simultaneously or successively, in which case it does not matter which of the two components is applied first. The ammonium or metal salts optionally present may be added to the first or second component. A time of up to 30 minutes can elapse between application of the first and second components. The fibers may even be pretreated with the salt solution.

The compounds of formula I and the oxidation dye precursors, color 110 intensifiers and substantive dyes optionally present may be stored either separately or together either in the form of a liquid or paste-like preparation (aqueous or water-free) or as a dry powder. Where the components are stored separately, they are mixed thoroughly together only shortly before application. Where the components are stored as a dry powder, a defined quantity of warm water (30 to 80° C.) is normally added and a homogeneous mixture prepared before application.

EXAMPLES

Coloring

A cream base with the following composition [all quantities in g unless otherwise indicated] was first prepared:

| | |
|---|---|
| tallow fatty alcohol | 17.0 |
| Lorol ® techn.[1] | 4.0 |
| Texapon ® N 28[2] | 40.0 |
| Dehyton ® K[3] | 25.0 |
| Eumulgin ® B 2[4] | 1.5 |
| Distilled water | 12.5 |

[1]$C_{12-18}$ fatty alcohol (Cognis)
[2]sodium lauryl ether sulfate (ca. 28% active substance; CTFA name: Sodium Laureth Sulfate) (Cognis)
[3]fatty acid amide derivative of betaine structure with the formula: R—$CONH(CH_2)_3N^+(CH_3)_2CH_2COO$ (ca. 30% active substance; CTFA name: Cocoamidopropyl Betaine (Cognis)
[4]cetyl stearyl alcohol containing ca. 20 mol EO (CTFA name: Ceteareth-20) (Cognis)

The following hair coloring cream emulsion was then prepared on the basis of this cream:

| cream base: | 50.0 |
|---|---|
| coloring component | 7.5 mmol |
| Na$_2$SO$_3$ (inhibitor) | 1.0 |
| (NH$_4$)$_2$SO$_4$ | 1.0 |
| conc. ammonia solution | to pH 10 |
| water | to 100 |

The constituents were mixed in the above order. After addition of the oxidation dye precursors and the inhibitor, the emulsion was first adjusted to pH 10 with concentrated ammonia solution and then made up with water to 100 g.

The coloring cream was applied to ca. 5 cm long tresses of standardized, 90% gray but not specially pretreated human hair and left thereon for 30 minutes at 32° C. On completion of the coloring process, the hair was rinsed, washed with a standard shampoo and then dried.

The coloring components used and the coloring results are set out in the following Table:

| Coloring component | Color |
|---|---|
| Compound 1 in Table 1 | Calypso red |
| Compound 2 in Table 1 | Melon orange |
| Compound 3 in Table 1 | Lemon yellow |
| Compound 4 in Table 1 | Cream |
| Compound 5 in Table 1 | Red-orange |
| Compound 6 in Table 1 | Red |

What is claimed is:

1. A method for coloring keratin-containing fibers comprising applying a coloring composition containing a coloring component compound of the formula (I):

wherein =B— is the group =CR$^1$— or the group

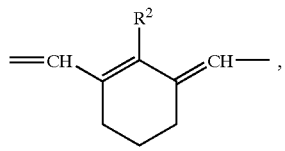

A is selected from the group consisting of

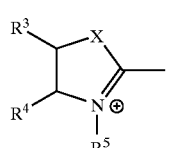
A1

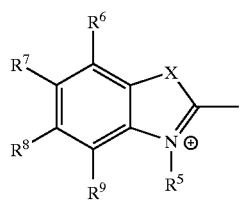
A2

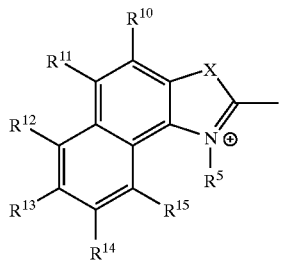
A3

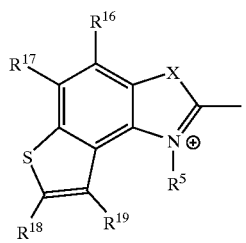
A4 and A' is selected from the group consisting of

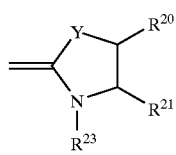
A11

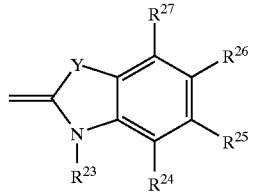
A12

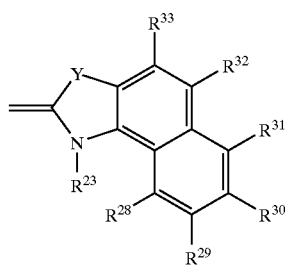
A13

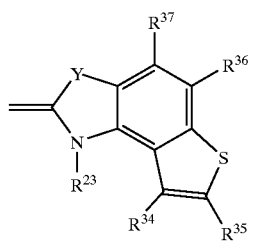
A14 wherein
X and Y independently of one another are selected from the group consisting of a sulfur atom, an oxygen atom or a group NR', where R' is a C$_{1-4}$ alkyl group optionally substituted by an SO$_3^-$group,
R$^1$ is selected from the group consisting of hydrogen, a C$_{1-4}$ alkyl group or an NH$_2$ group, $R^2$ is hydrogen or a halogen atom, $R^5$ and $R^{23}$ independently of one another are selected from the group consisting of a methyl group, an ethyl group, a hydroxyethyl group, a 2-sulfonate propyl group and a 3-sulfonate propyl group, the positive charge being compensatable by an acid anion, $R^8$, $R^{17}$, $R^{25}$ and $R^{26}$ independently of one another are selected from the group consisting of hydrogen, a $C_{1-4}$ alkyl group, a $C_{1-4}$ alkoxy group, a phenyl group, an $SO_2CF_3$ group or a carboxy group esterified with a $C_{1-4}$ alkyl group and $R^3$, $R^4$, $R^6$, $R^7$, $R^{9-16}$, $R^{18-21}$, $R^{24}$ and $R^{27-37}$ independently of one another are selected from the group consisting of hydrogen, a halogen atom, a $C_{1-4}$ alkyl group or a $C_{1-4}$ alkoxy group optionally substituted by one or more hydroxy groups or halogen atoms, the positive charge being compensatable by a negative charge in one of the substituents or by an acid anion.

2. The method of claim 1 wherein $R^8$, $R^{17}$, $R^{25}$ and $R^{26}$ independently of one another are selected from the group consisting of hydrogen, a methyl group, an ethyl group, a methoxy group, a phenyl group, an $SO_2CF_3$ group or a carboxyethyl group.

3. The method of claim 1 wherein $R^2$ is a chlorine group.

4. The method of claim 1 wherein the acid anion group is a $SO_3^-$ group.

5. The method of claim 1 wherein said composition further contains color intensifiers selected from the group consisting of piperidine, piperidine-2-carboxylic acid, piperidine-3-carboxylic acid, piperidine-4-carboxylic acid, pyridine, 2-hydroxypyridine, 3-hydroxypyridine, 4-hydroxypyridine, imidazole, 1-methyl imidazole, histidine, pyrrolidine, proline, pyrrolidone, pyrrolidone-5-carboxylic acid, pyrazole, 1,2,4-triazole and piperazidine or mixtures thereof.

6. The method of claim 1 wherein said composition further contains substantive dyes selected from the group consisting of nitrophenylenediamines, nitroaminophenols, anthraquinones and indophenols and wherein said dyes are present in a quantity of 0.01 to 20% by weight, based on the composition as a whole.

7. The method of claim 1 wherein said composition further contains ammonium or metal salts selected from the group consisting of formates, carbonates, halides, sulfates, butyrates, valerates, caproates, acetates, lactates, glycolates, tartrates, citrates, gluconates, propionates, phosphates and phosphonates of alkali metals, alkaline earth metals or aluminum, manganese, iron, cobalt, copper or zinc.

8. The method of claim 1 which further contains oxidizing agents in a quantity of 0.01 to 6% by weight, based on the solution applied.

9. The method of claim 1 which further contains anionic, zwitterionic or nonionic surfactants.

10. The method of claim 1 wherein A is A1, X is S, $R^5$ is $CH_3$, B is =CH— A' is A14, Y is S and $R^{23}$ is $C_2H_5$ or 3-Sulfonatepropyl and if necessary the counterion is iodide.

11. The method of claim 1 wherein A is A1, X is S, $R^5$ is $CH_3$, B is =CH—, A' is A12, Y is S and $R^{23}$ is $C_2H_5$ or 3-Sulfonatepropyl and if necessary the counterion is iodide.

12. The method of claim 1 wherein A is A1, X is S, $R^5$ is $CH_3$, B is =CH—, A' is A13, Y is S and $R^{23}$ is $C_2H_5$ or 3-Sulfonatepropyl and if necessary the counterion is iodide.

13. The method of claim 1 wherein A is A3, X is S, $R^5$ is 3-Sulfonatepropyl, B is CR1 wherein R1 is $CH_3$ or $C_2H_5$, A' is A12 where $R^{25}$ is OCH3, A13 or A14, Y is S and $R^{23}$ is $CH_3$, 3-Sulfonatepropyl or $C_2H_5$ and if necessary the counterion is pyridinium or triethylammonium.

14. The method of claim 1 wherein A is A2, X is S, $R^5$ is 3-Solfonatepropyl, B is $CNH_2$, A' is A12, Y is S and $R_{23}$ is 3-Sulfonatepropyl and if necessary the counterion is Ammonium.

15. The method of claim 1 wherein A is A2 wherein $R^8$ is $COOC_2H_5$, X is N—$C_2H_5$, $R^5$ is $C_2H_5$, 8 is =CH—, A' is A12 wherein $R^{26}$ is COO $C_2H_5$, Y is (3-Sulfonatepropyl)-N and $R^{23}$ is $C_2H_5$.

16. The method of claim 1 wherein A is A2 wherein $R^8$ is $SO_2CF_3$, X is N—$C_2H_5$, $R^5$ is $C_2H_5$, B is =CH—, A' is A12 wherein $R^{25}$, is $SO_2CF_3$, Y is N—$C_2H_5$, $R^{23}$ is $C_2H_5$ and if necessary the counterion is iodide.

17. The method of claim 1 wherein A is A2, X is S, $R^5$ is 2-Hydroxyethyl, B is $CCH_3$, A' is A12, Y is S, $R^{23}$ is 2-Hydroxyethyl and if necessary the counterion is chloride.

18. The method of claim 1 wherein A is A4, X is S, $R^5$ is 3-Sulfonatepropyl, B is $CC_2H_5$, A' is A14, Y is S, $R^{23}$ is 3-Sulfonatepropyl and if necessary the counterion is pyridinium.

19. The method of claim 1 wherein A is A4 wherein $R^{17}$ is $OCH_3$, X is S, $R^5$ is 3-Sulfonatepropyl, B is C $C_2H_5$, A' is A12 wherein $R^{25}$ is phenyl, Y is S, $^{23}$ is 3-Sulfonatepropyl and if necessary the counterion is triethylammonium.

20. The method of claim 1 wherein A is A4, X is S, $R^5$ is 3-Sulfonatepropyl, B is C $C_2H_5$, A' is A12 wherein $R^{25}$ is $OCH_3$, Y is S and $R^{23}$ is $C_2H_5$.

21. The method of claim 1 wherein A is A2 wherein $R^8$ is phenyl, X is O, $R^5$ is $C_2H_5$, B is C $C_2H_5$, A' is A12 wherein $R^{25}$ is phenyl, Y is O, $R^{23}$ is $C_2H_5$ and if necessary the counterion is ethylsulfate.

22. The method of claim 1 wherein A is A1, X is S, $R^5$ is $C_2H_5$, B is =CH—, A' is A11, Y is S, $R^{23}$ is $C_2H_5$ and if necessary the counterion is iodide.

23. The method of claim 1 wherein A is A2 where $R^8$ is $OCH_3$, X is S, $R^5$ is 2-hydroxyethyl, B is C $C_2H_5$, A' is A12 wherein $R^{25}$ is $OCH_3$, Y is S, $R^{23}$ is 2-hydroxyethyl and if necessary the counterion is 4-methylbenzenesulfonate.

24. The method of claim 1 wherein A is A2 where $R^8$ is phenyl, X is O, $R^5$ is $C_2H_5$, B is $CCH_3$, A' is A12 where $R^{25}$ is phenyl, Y is O, $R^2$ is $C_2H_5$ and if necessary the counterion is ethylsulfate.

25. The method of claim 1 wherein A is A2, X is S, $R^5$ is $C_2H_5$, B is $CCH_3$, A' is A12, Y is S, $R^{23}$ is $C_2H_5$ and if necessary the counterion is iodide.

26. The method of claim 1 wherein A is A2 where $R^8$ is phenyl, X is O, $R^5$ is 3-Sulfonatepropyl, B is C $C_2H_5$, A' is A12 where $R^{25}$ is phenyl, Y is O, $R^{23}$ is 3-sulfonatepropyl and if necessary the counterion is pyridinium.

27. The method of claim 1 wherein A is A2, X is S, $R^5$ is $C_2H_5$, B is

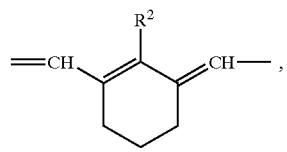

A' is A12, Y is S, $R^{23}$ is $C_2H_5$ and if necessary the counterion is iodide.

* * * * *